United States Patent
Zhao et al.

(10) Patent No.: US 10,767,206 B2
(45) Date of Patent: Sep. 8, 2020

(54) NITROGEN SOURCE FEEDING FERMENTATION PROCESS FOR PRODUCING GELLAN GUM

(71) Applicant: DSM IP ASSETS B.V., TE Heerlen (NL)

(72) Inventors: Jie Zhao, Shanghai (CN); Zhihui Gao, Shanghai (CN); Wouter Adrianus Van Winden, AA Echt (NL); Rogier Meulenberg, AA Echt (NL)

(73) Assignee: DSM IP ASSETS B.V., Te Heerlen (NL)

( * ) Notice: Subject to any disclaimer, the term of this patent is extended or adjusted under 35 U.S.C. 154(b) by 30 days.

(21) Appl. No.: 16/012,653

(22) Filed: Jun. 19, 2018

(65) Prior Publication Data

US 2019/0002938 A1 Jan. 3, 2019

(30) Foreign Application Priority Data

Jun. 29, 2017 (CN) .......................... 2017 1 0518726

(51) Int. Cl.
*C12P 19/04* (2006.01)
(52) U.S. Cl.
CPC .................................. *C12P 19/04* (2013.01)
(58) Field of Classification Search
None
See application file for complete search history.

(56) References Cited

U.S. PATENT DOCUMENTS 7,645,600 B2 * 1/2010 Yamazaki ............... C12P 19/04
435/183

FOREIGN PATENT DOCUMENTS

| CN | 101240307 A | | 8/2008 |
| CN | 103834708 | * | 3/2014 |
| CN | 107805649 A | | 3/2018 |

OTHER PUBLICATIONS

Banik et al. Bioresource Technology 98 (2007) 792-797 (Year: 2007).*
Wu et al. Shipin Gongye Keji (2013), 34(10), 395-399 (Abstract) (Year: 2013).*
Dreveton, E. et al., "Effect of Mixing and Mass Transfer Conditions on Gellan Production by Auromonas Elodea", Journal of Fermentation and Bioengineering, vol. 77, No. 6, 1993, pp. 642-649.
Extended European Search Report, EP 18178361.4, dated Nov. 27, 2018.
Giavasis, I. et al., "Gellan Gum", Critical Reviews in Biotechnology, 20:3, 177-211 (2000).

* cited by examiner

*Primary Examiner* — Christian L Fronda
(74) *Attorney, Agent, or Firm* — Maschoff Brennan; Brent A. Johnson; Yuefen Zhou

(57) ABSTRACT

The invention provides a new fermentation process for producing gellan gum, which can control the feeding amount and feeding speed of the nitrogen sources accurately and quantitatively, and control the growth and gum production of the strains, so as to significantly improve the controllability, stability and yield of the fermentation process for producing gellan gum.

6 Claims, 2 Drawing Sheets

NITROGEN SOURCE FEEDING FERMENTATION PROCESS FOR PRODUCING GELLAN GUM

CROSS-REFERENCE TO RELATED APPLICATION

This application claims priority to the Chinese No. 201710518726.8, filed Jun. 29, 2017, which is incorporated by reference by its entirety.

TECHNICAL FIELD

The invention is related to the field of fermentation. Particularly, the invention is related to a fermentation process for producing gellan gum.

BACKGROUND

Microbial gum is one of the important sources of gums. Microbial gums obtained by fermentation can be used in many aspects, like food additives. As a new kind of microbial gum, gellan gum has been paid more and more attention.

Most of the existing processes for producing gellan gum are carried out by batch fermentation, and organic nitrogen sources, such as insoluble soybean powder, are normally used to control production rate of strains because of the slow-release nitrogen therein. However, insolubility and unstable quality of the soybean powder can cause variations in fermentation process, so quality of the final products is not stable. On the other hand, inorganic nitrogen sources, such as aqueous ammonia or $NH_4Cl$, usually cause low production rate in batch fermentation and thus are not suitable for industrial application.

Therefore, a new fermentation process for producing gellan gum is desirable.

DETAILED DESCRIPTION

The invention provides a new fermentation process for producing gellan gum. In particular, the fermentation process of the present invention comprises feeding a nitrogen source in an effective amount into broth during the fermentation.

In the invention, the broth is a culture medium inoculated with strains capable of producing gellan gum product. The strain includes but is not limited to *Sphingomonas paucimobilis, Sphingomonas Azotofigens* and *Sphingomonas elodea*.

The culture medium is any medium suitable for the strains above to produce gellan gum. As known in the art, besides the strains, the culture medium may also contain carbon sources (one or more of conventional sugars such as glucose, sucrose, maltose and fructose syrup), nitrogen sources, phosphate and other inorganic salts (see: Ioannis Giavasis etc., Critical Reviews in Biotechnology, 20(3): 177-211 (2000)). Preferably, the culture medium contains no nitrogen source, or a small amount of nitrogen source.

In the invention, the nitrogen source may be any nitrogen source suitable for culturing the strains for producing gellan gum in the culture medium, and the examples include but are not limited to one or more of nitrogen-containing materials such as glutamic acid, monosodium glutamate, aqueous ammonia, $(NH_4)_2SO_4$, $NaNO_3$, $KNO_3$, $NH_4NO_3$, $NH_4Cl$, yeast extract, $(NH_4)_3PO_4$, $(NH_4)_2HPO_4$, $NH_4H_2PO_4$, $NH_4OH$, and soybean powder etc. According to its nitrogen content, the nitrogen source may be prepared to certain concentrations and sterilized for use. In the invention, the nitrogen source fed into the broth during the fermentation may be the same as or different from the nitrogen source contained in the culture medium.

In the invention, the "effective amount" refers to an amount which can meet the production requirement of the strains and achieve the optimum growth curve of the strains. Preferably, the "effective amount" refers to the total amount of the fed nitrogen, which, based on the total volume of the broth, may be 0.01-0.1 mol/L, more preferably 0.015-0.08 mol/L, even more preferably 0.02-0.04 mol/L (calculated by nitrogen element in the broth).

In the invention, the nitrogen source may be fed in an appropriate manner, for example, in any one of below manners, into the broth during the fermentation after inoculation with the strain:

1) the nitrogen source is intermittently fed into the broth in a pulsed feeding mode at certain intervals;
2) the nitrogen source is continuously fed into the broth with a constant feeding speed and the feeding speed is kept constant during the whole fermentation;
3) the nitrogen source is continuously fed into the broth with a constant feeding speed and the feeding speed is kept higher in early stage and lower in late stage, or vice versa, during the fermentation;
4) the nitrogen source is continuously fed into the broth with a constant feeding speed and it is fed in early stage while not in late stage, or vice versa, during the fermentation;
5) The nitrogen source is continuously fed into the broth with an exponentially changing feeding speed; and
6) The nitrogen source is continuously fed into the broth with a linearly changing feeding speed.

Preferably, the nitrogen source is fed into the broth during the fermentation after inoculation with the strain according to a F(T)-F(N) feeding curve, which falls into the shaded area of the feeding curves diagram as given in FIG. 1.

More preferably, the nitrogen source is fed into the broth during the fermentation after inoculation with the strain according to the F(T)-F(N) feeding curve which is given in FIG. 2.

In one embodiment, the fermentation process of the present invention comprises following steps:

1) inoculating culture medium of the present invention with any strain of the present invention;
2) initiating the fermentation, and feeding the nitrogen source in the effective amount as disclosed in the present invention into broth during the fermentation; and
3) stopping the fermentation, and isolating and purifying the gellan gum produced during the fermentation.

Inoculation with strain, fermentation, and isolation and purification of the obtained gellan gum are known in the art, so it is not described furtherly in the present application. For the details, please see: Ioannis Giavasis etc., Critical Reviews in Biotechnology, 20(3): 177-211 (2000).

The fermentation process of the present invention can control the feeding amount and feeding speed of the nitrogen sources both accurately and quantitatively, and thereby control the growth and gum production of the strains, so as to significantly improve the controllability, stability and yield of the fermentation process for producing gellan gum.

DESCRIPTION OF THE FIGURES

FIG. 1: preferable F(T)-F(N) feeding curves diagram during fermentation, wherein:

Figure 2:
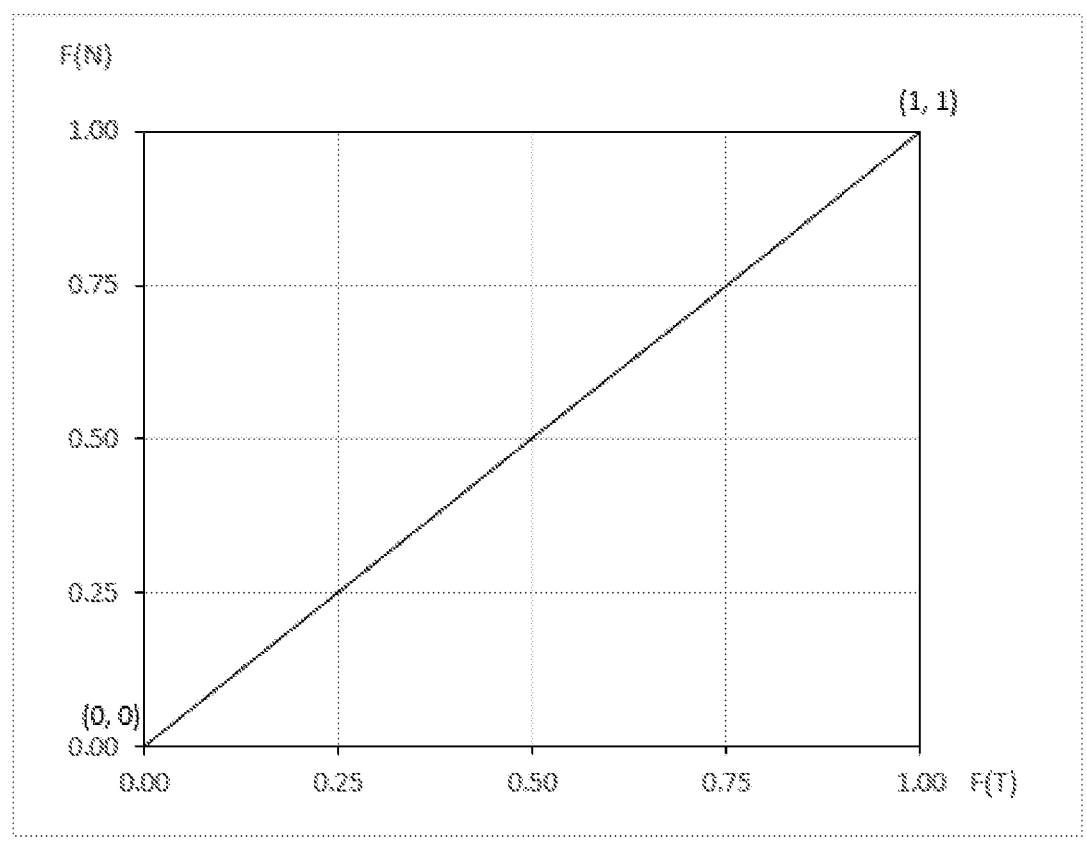

F(T)=Time elapsed after the start of the fermentation/Total time of Fermentation F(N)=Cumulative amount of nitrogen source fed since the start of the fermentation/Total amount of nitrogen source fed at the end of the fermentation;

FIG. 2: more preferable F(T)-F(N) feeding curve during fermentation, wherein:

F(T)=Time elapsed after the start of the fermentation/Total time of Fermentation F(N)=Cumulative amount of nitrogen source fed since the start of the fermentation/Total amount of nitrogen source fed at the end of the fermentation.

EXAMPLES

The invention is further illustrated by the following examples. The Examples are only for explanation and are not intended to limit the scope of the invention.

Example 1

1. Preparation of Culture Medium

Seed culture medium: Seed culture medium was prepared according to the following composition: 7 g/kg yeast extract, 25 g/kg sucrose, 0.5 g/kg $KH_2PO_4$, 0.75 g/kg $K_2HPO_4$ and 0.6 g/kg $MgSO_4.7H_2O$. The pH was adjusted to 7.0±0.1 and the culture medium was sterilized.

Fermentation culture medium: 7.5 L fermentation culture medium was prepared in a 12 L fermenter according to the following composition: 15 g/kg glucose, 0.5 g/kg $KH_2PO_4$, 0.5 g/kg $K_2HPO_4$, 0.375 g/kg $MgSO_4.7H_2O$, 0.5 g/kg trace elements solution (5 g/kg Citric acid.$1H_2O$, 0.20 g/kg $H_3BO_3$, 0.20 g/kg $CuCl_2.2H_2O$, 0.20 g/kg $NiCl_2.6H_2O$, 0.60 g/kg $MnSO_4.1H_2O$, 0.025 g/kg $Na_2MoO_4.2H_2O$, 1.0 g/kg $ZnSO_4.7H_2O$, 8 g/kg $FeSO_4.7H_2O$) and 0.15 g/kg antifoaming agent. The pH was adjusted to 7.0±0.1 and the culture medium was sterilized.

2. Nitrogen Source 500 mL nitrogen source solution containing 9.113 g mono sodium glutamate and 9.263 g liquid yeast extract was prepared and sterilized according to the conventional methods.

3. Activation of the Strain

The strain *Sphingomonas azotofigens* (Zhejiang DSM Zhongken Biotechnology Co., Ltd.) was inoculated into a 500 mL flask containing 60 mL of the sterilized seed culture medium. After shaking at 200 rpm and 30° C. for 16 h, 0.6 g culture was transferred into a 2 L flask containing 450 g of the sterilized seed culture medium. After culturing at 200 rpm and 30° C. for 16 h, the second culture was used as seed culture for the main fermentation.

4. Fermentation Process 375 g seed culture was transferred into the main fermentation culture medium. The fermentation process was carried out and nitrogen source was fed at a constant speed according to the following parameters:

| Process parameters | Duration | Control parameters |
| --- | --- | --- |
| Temperature [° C.] | 0-EOF* | 30.0 ± 0.1 |
| Aeration (L/min) | 0-12 | 4.0 |
|  | 12-EOF* | 8.0 |
| pH | 0-EOF* | 7.0 ± 0.1 |
| Agitation [rpm] | 0-24 | 600 → 1000 |
|  | 24-EOF* | 1000 |
| Feed rate of nitrogen solution (g/kg/h) | 0-EOF* | 1.39 |

*EOF: end of fermentation = 48 h

5. Fermentation Result

After 48 h of fermentation, the crude gellan concentration reached 5.36 g/kg (determined by ethanol precipitation known in the art), and the viscosity reached 4730 cp.

Viscosity measurement of fermentation broth: the viscosity of fresh broth sample was directly measured with a rheometer (Anton Paar MCR 301) with the CP50-1 spindle for 5 minutes under a constant shear rate of 10 $s^{-1}$ and a constant temperature of 30° C.

Example 2

The Fermentation was carried out the same as example 1, except that 500 mL solution containing 7.3 g of 25% aqueous ammonia was used as nitrogen source solution.

Result of fermentation indicated that the crude gellan concentration reached 4.99 g/kg (determined by ethanol precipitation known in the art) and the viscosity reached 4635 CP (viscosity measurement was the same as Example 1).

Example 3

The Fermentation was carried out the same as example 2, except that nitrogen source solution was fed at different speeds in different stages: 0-16 h, 2.1 g/kg/h; 17-32 h, 1.4 g/kg/h; 33-48 h, 0.7 g/kg/h.

Result of fermentation indicated that the crude gellan concentration reached 4.82 g/kg (determined by ethanol precipitation known in the art) and the viscosity reached 4400 CP (viscosity measurement was the same as Example 1).

Example 4

1. Seed culture medium was prepared and the strain was activated the same as example 1.
2. Fermentation culture medium: 7.5 L fermentation culture medium was prepared in a 12 L fermenter according to the following composition: 15 g/kg glucose, 1.215 g/kg monosodium glutamate, 1.235 g/kg yeast extract, 0.5 g/kg $KH_2PO_4$, 0.5 g/kg $K_2HPO_4$, 0.375 g/kg $MgSO_4.7H_2O$, 0.5 g/kg trace elements solution (5 g/kg Citric acid.$1H_2O$, 0.20 g/kg $H_3BO_3$, 0.20 g/kg $CuCl_2.2H_2O$, 0.20 g/kg $NiCl_2.6H_2O$, 0.60 g/kg $MnSO_4.1H_2O$, 0.025 g/kg $Na_2MoO_4.2H_2O$, 1.0 g/kg $ZnSO_4.7H_2O$, 8 g/kg $FeSO_4.7H_2O$) and 0.15 g/kg antifoaming agent. The pH was adjusted to 7.0±0.1 and the culture medium was sterilized.
3. Fermentation Process The fermentation process was carried out the same as example 1, except for no feeding of nitrogen source during the whole fermentation.

| Process parameters | Duration | Control parameters |
| --- | --- | --- |
| Temperature [° C.] | 0-EOF* | 30.0 ± 0.1 |
| Aeration (L/min) | 0-12 | 4.0 |
|  | 12-EOF* | 8.0 |
| pH | 0-EOF* | 7.0 ± 0.1 |
| Agitation [rpm] | 0-24 | 600 → 1000 |
|  | 24-EOF* | 1000 |

*EOF: end of fermentation

4. Fermentation Result

After 48 h of fermentation, the crude gellan concentration reached 2.5 g/kg (determined by ethanol precipitation known in the art), and viscosity reached 1800 CP (viscosity measurement was the same as Example 1).

Example 5

1. Seed culture medium was prepared and the strain was activated the same as example 1.
2. Fermentation culture medium: 7.5 L fermentation culture medium was prepared in a 12 L fermenter according to the following composition: 15 g/kg glucose, 0.87 g/kg monosodium glutamate, 0.88 g/kg yeast extract, 0.5 g/kg $KH_2PO_4$, 0.5 g/kg $K_2HPO_4$, 0.375 g/kg $MgSO_4 \cdot 7H_2O$, 0.5 g/kg trace elements solution (5 g/kg Citric acid.$1H_2O$, 0.20 g/kg $H_3BO_3$, 0.20 g/kg $CuCl_2 \cdot 2H_2O$, 0.20 g/kg $NiCl_2 \cdot 6H_2O$, 0.60 g/kg $MnSO_4 \cdot 1H_2O$, 0.025 g/kg $Na_2MoO_4 \cdot 2H_2O$, 1.0 g/kg $ZnSO_4 \cdot 7H_2O$, 8 g/kg $FeSO_4 \cdot 7H_2O$) and 0.15 g/kg antifoaming agent. The pH was adjusted to 7.0±0.1 and the culture medium was sterilized.
3. Nitrogen Source
300 mL nitrogen source solution containing 5.46 g mono sodium glutamate and 5.55 g liquid yeast extract was prepared and sterilized according to the conventional methods.
4. Fermentation Process
The fermentation was carried out the same as Example 1, except that the nitrogen source solution was fed at 0.4 g/kg/h.
5. Result of Fermentation
After 48 h of fermentation, the crude gellan concentration reached 4.9 g/kg (determined by ethanol precipitation known in the art), and viscosity reached 4200 cp (viscosity measurement was the same as Example 1).

Figure 1:
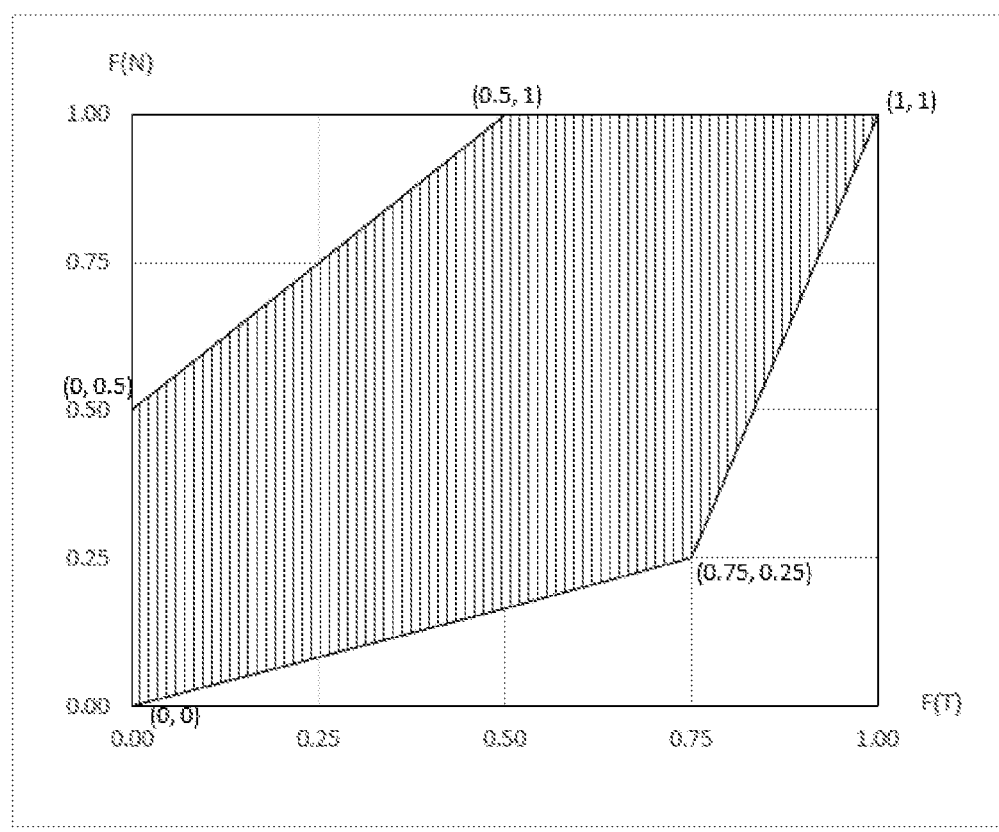

The invention claimed is:
1. A fermentation process for producing a gellan gum, comprising the following steps:
   1) inoculating a culture medium with a strain capable of producing a gellan gum to form a broth; and
   2) initiating a fermentation, and feeding a nitrogen source into the broth during the fermentation;
   wherein the strain capable of producing the gellan gum is selected from a group consisting of *Sphingomonas paucimobilis, Sphingomonas Azotofigens*, and *Sphingomonas elodea:*
   wherein the nitrogen source is fed into the broth during the fermentation after inoculation with the strain according to FIG. 1 feeding curve diagram, which falls into the shaded area of FIG. 1;
   wherein a total amount of the nitrogen source fed into the broth is 0.01 mol/L to 0.1 mol/L calculated as the nitrogen element in the broth in relative to the total volume of the broth.
2. The fermentation process of claim 1, wherein the nitrogen source is selected from the group consisting of the following one or more of nitrogen-containing materials: glutamic acid, monosodium glutamate, aqueous ammonia, $(NH_4)_2SO_4$, $NaNO_3$, $KNO_3$, $NH_4NO_3$, $NH_4Cl$, yeast extract, $(NH_4)_3PO_4$, $(NH_4)_2HPO_4$, $NH_4H_2PO_4$, $NH_4OH$, and soybean powder.
3. The fermentation process of claim 1, wherein the total amount of the nitrogen source fed into the broth is 0.015 mol/L to 0.08 mol/L, or 0.02 mol/L to 0.04 mol/L, which is calculated as the nitrogen element in the broth in relative to the total volume of the broth.
4. The fermentation process of claim 1, wherein the nitrogen source is fed in any one of below manners into the broth during the fermentation after inoculation with a strain:
   1) the nitrogen source is intermittently fed into the broth in a pulsed feeding mode at certain intervals;
   2) the nitrogen source is continuously fed into the broth with a constant feeding speed and the feeding speed is kept constant during the fermentation;
   3) the nitrogen source is continuously fed into the broth with a constant feeding speed, and the feeding speed is kept higher in an early stage and lower in a late stage, or the feeding speed is kept lower in an early stage and higher in a late stage, during the fermentation;
   4) the nitrogen source is continuously fed into the broth with a constant feeding speed, and it is fed in an early stage while not fed in a late stage, or it is not fed in an early stage while fed in a late stage, during the fermentation;
   5) the nitrogen source is continuously fed into the broth with an exponentially changing feeding speed; or
   6) the nitrogen source is continuously fed into the broth with a linearly changing feeding speed.
5. The fermentation process of claim 1, further comprising the following step:
   stopping the fermentation, and isolating and purifying the gellan gum produced during the fermentation.
6. The fermentation process of claim 1, wherein the culture medium contains no nitrogen source.

* * * * *